United States Patent [19]
Hoffman, Jr. et al.

[11] Patent Number: 4,731,368
[45] Date of Patent: Mar. 15, 1988

[54] THIENOPYRIDINE SULFONAMIDES AND THEIR OPHTHALMOLOGICAL FORMULATION

[75] Inventors: Jacob M. Hoffman, Jr.; Kenneth L. Shepard, both of North Wales, Pa.

[73] Assignee: Merck & Co., Inc., Rahway, N.J.

[21] Appl. No.: 939,389

[22] Filed: Dec. 8, 1986

[51] Int. Cl.$^4$ .................... A61K 31/44; C07D 495/04
[52] U.S. Cl. ..................................... 514/301; 546/114
[58] Field of Search ........................ 546/114; 514/301

[56] References Cited
U.S. PATENT DOCUMENTS
4,544,667 10/1985 Shepard et al. ..................... 514/470

FOREIGN PATENT DOCUMENTS
129478 12/1984 European Pat. Off. .
2081712 2/1982 United Kingdom .

Primary Examiner—Richard A. Schwartz
Assistant Examiner—Bernard J. Dentz
Attorney, Agent, or Firm—William H. Nicholson; Michael C. Sudol

[57] ABSTRACT

Thienopyridine sulfonamides are carbonic anhydrase inhibitors useful in the treatment of elevated intraocular pressure and disorders associated therewith such as glaucoma.

9 Claims, No Drawings

THIENOPYRIDINE SULFONAMIDES AND THEIR OPHTHALMOLOGICAL FORMULATION

SUMMARY OF THE INVENTION

This invention is concerned with novel compounds useful in the treatment of elevated intraocular pressure with the general structural formula:

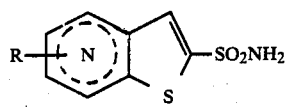

wherein the N indicates that the moiety is a pyrido, dihydropyrido or tetrahydropyrido ring with the nitrogen at the 4-, 5-, 6- or 7-position.

The invention is also concerned with novel pharmaceutical formulations comprising one of the novel compounds as active ingredient and a method of treating elevated intraocular pressure and disease states associated therewith such as glaucoma.

The invention is further concerned with novel processes for preparing the novel compounds.

BACKGROUND OF THE INVENTION

Glaucoma is an ocular disorder associated with elevated intraocular pressures which are too high for normal function and may result in irreversible loss of visual function. If untreated, glaucoma may eventually lead to blindness. Ocular hypertension, i.e. the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many β-adrenergic blocking agents are effective in reducing intraocular pressure. While many of these agents are effective in reducing intraocular pressure, they also have other characteristics, e.g. membrane stabilizing activity, that are not acceptable for chronic ocular use. (S)-1-tert-butylamino-3-[(4-morpholino-1,2,5-thiadiazol 3-yl)oxy]-2-propanol, a β-adrenergic blocking agent, was found to reduce intraocular pressure and to be devoid of many unwanted side effects associated with pilocarpine and, in addition, to possess advantages over many other β-adrenergic blocking agents, e.g. to be devoid of local anesthetic properties, to have a long duration of activity, and to display minimal tolerance.

Although pilocarpine, physostigmine and the β-blocking agents mentioned above reduce intraocular pressure, none of these drugs manifests its action by inhibiting the enzyme carbonic anhydrase and, thereby, impeding the contribution to aqueous humor formation made by the carbonic anhydrase pathway.

Agents referred to as carbonic anhydrase inhibitors, block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective. Despite the desirability of directing the carbonic anhydrase inhibitor only to the desired ophthalmic target tissue, no topically effective carbonic anhydrase inhibitors are available for clinical use.

However, topically effective carbonic anhydrase inhibitors are reported in U.S. Pat. Nos. 4,386,098; 4,416,890; and 4,426,388. The compounds reported therein are 5 (and 6) -hydroxy-2-benzothiazolesulfonamides and acyl esters thereof. European patent publication No. 129,478 discloses substituted benzo[b]thiophene-2-sulfonamides and U.S. Pat. No. 4,544,667 discloses substituted benzo[b]furan-2-sulfonamides as being useful in the treatment of elevated intraocular pressure.

DETAILED DESCRIPTION OF THE INVENTION

The novel compound of this invention has structural formula:

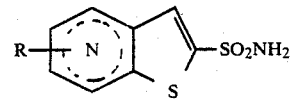

or N-oxide, or an ophthalmologically acceptable salt thereof wherein:

is a pyrido, dihydropyrido or tetrahydropyrido group with the N at the 4-, 5-, 6- or 7-position; and R is
(1) $C_{1-5}$ alkyl, either straight chain, branched chain or cyclic such as cyclopropyl,
(2) hydroxy-$C_{1-5}$ alkyl,
(3) —$OR^1$, wherein $R^1$ is hydrogen, $C_{1-3}$ alkyl including cyclopropyl, amino-$C_{1-3}$ alkyl, $C_{1-3}$ alkylamino-$C_{1-3}$ alkyl, di($C_{1-3}$alkyl)amino-$C_{1-3}$ alkyl, hydroxy-$C_{1-3}$ alkyl, or $C_{2-4}$ alkanoyl, $(O)_n$
(4) —S—$R^1$, wherein n is 0, 1 or 2,
(5) —$N(R^1)_2$ wherein the $R^1$ groups can be the same or different,
(6) halo such as chloro, bromo or fluoro,
(7) hydrogen,
(8) —$NO_2$, or
(9) oxo-; and if

represents a dihydro- or tetrahydropyrido-, the N can be substituted with $R^1$ or —$CONH_2$.

It is preferred that R be hydrogen, hydroxy or di ($C_{1-3}$ alkyl)amino-$C_{1-3}$ alkyl.

The novel processes of this invention comprise derivatization of the intact bicyclic ring systems which are known in the art.

The sulfonamide group, which is present in all of the novel compounds, is introduced by treating the corresponding lithium sulfinate with hydroxylamine-O-sulfonic acid in aqueous sodium acetate at or about room temperature for about 10 to 24 hours.

An alternate procedure comprises adding the corresponding sulfonyl chloride to ice cold ammonium hydroxide.

The pyrido-N-oxides are prepared by treatment with a per-acid such as m-chloroperbenzoic acid in an inert organic solvent at about 30°–50° C. over a period of about 10 to 24 hours.

Alternatively, the N-oxides are prepared by oxidation with 30% hydrogen peroxide in acetic acid at about 35°–60° C. for about 18–36 hours.

Compounds carrying an alkylamino group substituted on one of the pyrido carbons are prepared by treating the corresponding chloro-pyrido compound with the alkylamine at about 90°–120° C. for about 3 to 24 hours.

Dihydropyrido compounds are prepared by treating the corresponding tetrahydropyrido compound with activated manganese dioxide in an inert organic solvent at about 70°–90° C. over a period of about 6 to 10 hours.

N-carbamates of the tetrahydropyrido compounds are prepared by treatment with trimethylsilylisocyanate in an inert organic solvent at about 30°–50° C. for about 16 to 32 hours.

Treatment under similar conditions with ethylene oxide affords the N-hydroxyethyl derivative.

Hydroxy derivatives are prepared by treating a pyrido-N-oxide with acetic anhydride at reflux temperature for about 12 to 24 hours. It is advisable to protect the sulfamoyl group as the N,N-dimethyl formamidine during the reaction.

This invention is particularly concerned with formulations adapted for topical ocular administration for the treatment of glaucoma and other stages of elevated intraocular pressure and contain about 0.1% to 15% by weight of medicament, especially about 0.5 to 2% by weight of medicament, the remainder being comprised of carriers and other excipients well known in the art.

The medicament in the novel topical ocular formulations comprises one of the novel compounds of this invention either alone or in combination with a β-adrenergic blocking agent such as timolol maleate or a parasympathomimetic agent such as pilocarpine. In such combinations the two active agents are present in approximately equal amounts.

The novel method of treatment of this invention comprises the treatment of elevated intraocular pressure by the administration of a novel compound of this invention or a pharmaceutical formulation thereof. Of primary concern is the treatment by topical ocular administration of about 0.1 to 25 mg and especially 0.2 to 10 mg of such compound per day, either by single dose or on a 2 to 4 dose per day regimen.

The utility of the novel compounds was determined from the observation that the intraocular pressure (IOP) of the α-chymotrypsinized rabbit eye was significantly lowered by the bilateral instillation of solutions of a representative number of the compounds shown in the following table:

EFFECT OF TOPICALLY ADMINISTERED DRUG ON THE α-CHYMOTRYPSIN-INDUCED ELEVATION OF IOP IN THE RABBIT[a]

General structure: R—(pyridine ring fused to thiophene)—$SO_2NH_2$

| TEST COMPOUND | DOSE (%)[b] | MAX. IOPΔ (mm Hg)[c] |
|---|---|---|
| thieno[2,3-c]pyridine-2-sulfonamide | 0.5% suspension<br>0.1% solution | −6.5<br>−6.2 |
| thieno[3,2-c]pyridine-2-sulfonamide | 0.5% suspension | −6.2 |
| thieno[2,3-b]pyridine-2-sulfonamide | 0.5% suspension | −4.0 |
| hydroxy-thieno[2,3-b]pyridine-2-sulfonamide | 0.5% suspension | −5.0 |
| hydroxy-thieno[2,3-c]pyridine-2-sulfonamide | 0.5% suspension | −3.8 |

[a] Rabbits were pretreated with α-chymotrypsin at least 1 month previously in right eye only. Compound or vehicle (0.5% HEC) was instilled (50 μl) into both eyes. For full protocol see Sugrue et al., J. Pharm. Exp. Ther., 232, 534 (1985).
[b] A single 50 μl drop of the test compound was applied topically as a formulation of the indicated % concentration in freshly prepared hydroxyethylcellulose (HEC) vehicle.
[c] The reported number is the maximum, statistically significant drop in IOP recorded during the 5 hour duration of the assay.

EXAMPLE 1

2-Sulfamoylthieno[2,3-c]pyridine

To a solution of thieno[2,3-c]pyridine (7.6 g, 56 mmol) in tetrahydrofuran (80 ml) which was cooled to −70° C., under a nitrogen atmosphere, was added dropwise 0.5 M lithium diisopropylamide in THF (130 ml, 65 mmol) to give a gummy suspension. The suspension was warmed to −30° C. for ½ hour. The mixture was recooled to −70° C. and sulfur dioxide gas was passed over the reaction mixture to give a yellow precipitate. This suspension was warmed to room temperature and diluted with hexane (200 ml). The suspension was collected by filtration, washed with diethyl ether and dried giving 18.4 g of the lithium sulfinate intermediate.

This salt was dissolved in water (200 ml) and cooled to 0° C. Sodium acetate trihydrate (36 g, 0.44 mol) was added to this solution. Then hydroxylamine-O-sulfonic acid (19 g, 0.165 mol) was added and the solution was allowed to warm to room temperature overnight as the product precipitated. The precipitate was collected by filtration and dissolved in ethyl acetate/methanol. The solution was dried over anhydrous sodium sulfate and filtered through a pad of charcoal. The evaporated solution yielded 8.95 g (74.7% yield) of product. This was recrystallized from hot ethyl acetate to give white crystals (6.76 g); m.p. 191°–193° C.

Analysis calculated for $C_7H_6N_2O_2S_2$: N, 13.08; C, 39.24; H, 2.82. Found N, 13.03; C, 39.42; H, 2.86.

EXAMPLE 2

2-Sulfamoylthieno[2,3-c]pyridine (Alternate Procedure)

To a solution of potassium ferricyanide (76 g, 0.23 mol) in water (400 ml) was added a solution of potassium hydroxide (68 g, 0.113 mol) in water (150 ml), followed by a suspension of 2-sulfamoyl-4,5,6,7-tetrahydrothieno[2,3-c]pyridine (10.8 g, 49.5 mmol) in water (50 ml). This mixture was warmed at 80° C. for 4–6 hours. This solution was acidified with concentrated hydrochloric acid and then made basic with saturated sodium carbonate solution. The product was extracted from this solution with ethyl acetate. The ethyl acetate solution was dried over anhydrous sodium sulfate, filtered through a pad of charcoal and evaporated to give 5.5 g of crude product. This material was chromatographed on silica gel and eluted with ethyl acetate to give 3.7 g (34.9% yield) of pure product; m.p. 191°–193° C.

EXAMPLE 3

2-Sulfamoylthieno2,3-c]pyridine-6-oxide

To a warmed (40° C.) solution of 2-sulfamoylthieno[2,3-c]pyridine (3.83 g, 18 mmol) in methanol (30 ml) and ethyl acetate (45 ml) was added dropwise a solution of m-chloroperbenzoic acid (5.4 g, 25 mmol) in ethyl acetate (35 ml). After stirring for 2–4 hours, the precipitated product was collected by filtration. Evaporation of the filtrate yielded additional material. The crops of product were combined and digested in acetone to remove impurities. The material (3.98 g) remaining was recrystallized by dissolution in a minimum amount of hot dimethyl sulfoxide and dilution with ethanol. The pure product melted at 251°–253° C. (3.16 g, 76% yield).

Analysis calculated for $C_7H_6N_2O_3S_2$: N, 12.17; C, 36.51; H, 2.63. Found N, 11.92; C, 36.68; H, 2.79.

EXAMPLE 4

2-Sulfamoyl-6-acetyl-4,5,6,7-tetrahydrothieno[2,3-c]pyridine

To a solution of 6-acetyl-4,5,6,7-tetrahydrothieno[2,3-c]pyridine (6.1 g, 33.7 mmol) in methylene chloride (50 ml) containing acetic anhydride (9.8 ml, 102 mmol), which was cooled to 0° C., was added dropwise concentrated sulfuric acid (2.1 ml, 35.7 mmol). The gummy precipitate was vigorously stirred for 3–18 hours to give a fine powder. This suspension was diluted with diethyl ether and the intermediate sulfonic acid precipitate was collected by filtration and re-suspended in methylene chloride (65 ml). Under a nitrogen atmosphere, phosphorus pentachloride (9.8 g, 46 mmol) was added. This mixture was stirred for 3–20 hours to give a yellowish-green solution. Ice/water was then added and the two phase mixture was stirred for one hour. The methylene chloride layer was separated, dried over anhydrous sodium sulfate, and filtered through a pad of charcoal. The yellow filtrate was evaporated to dryness to give 8.4 g of crude sulfonyl chloride intermediate. This material was dissolved in acetone (25 ml) and added dropwise to an ice cooled solution of concentrated ammonium hydroxide (15 ml) and acetone (15 ml). After one hour, the precipitated product was collected by filtration. This product was washed with water, ethanol and diethyl ether to give 3.3 g of material. The combined washings and filtrates were concentrated and extracted with ethyl acetate to give additional product (1.2 g). The overall yield was 51%. Recrystallization from a large volume of hot methanol gave pure product; m.p. 253°–255° C.

Analysis calculated for $C_9H_{12}N_2O_3S_2$: N, 10.76; C, 41.52; H, 4.65. Found: N, 10.83; C, 41.82; H, 4.79.

EXAMPLE 5

2-Sulfamoyl-4,5,6,7-tetrahydrothieno[2,3-c]pyridine

A suspension of 2-sulfamoyl-6-acetyl-4,5,6,7-tetrahydrothieno[2,3-c]pyridine (9.61 g, 37 mmol) in 20% sodium hydroxide solution (75 ml) was warmed at 80° C. for 3 hours. The resultant clear solution was cooled, acidified with concentrated hydrochloric acid, and then made basic with saturated sodium carbonate solution. The product was isolated by exhaustive extraction into ethyl acetate/methanol. The dried solution was evaporated to give 7.36 g (91% yield) of product. Recrystallization from ethyl acetate/methanol gave pure product; m.p. 172°–175° C.

Analysis calculated for $C_7H_{10}N_2O_2S_2$: N, 12.84; C, 38.51; H, 4.62. Found: N, 12.86; C, 38.82; H, 4.62.

EXAMPLE 6

2-Sulfamoyl-4,5-dihydrothieno[2,3-c]pyridine

To a partial suspension of 2-sulfamoyl-4,5,6,7-tetrahydrothieno[2,3-c]pyridine (3.05 g, 14 mmol) in ethyl acetate (200 ml) was added activated manganese dioxide (3.0 g). This mixture was warmed to 80° C. Every two hours an additional 3.0 g of activated manganese dioxide was added until 12 g total had been added. This mixture was filtered hot and the collected manganese dioxide was re-extracted with hot ethyl acetate. The combined ethyl acetate extracts were evaporated to give 2.1 g of crude product. This material was purified by chromatography on silica gel eluting with a gradient 0–5% methanol/ethyl acetate. Recrystallization from ethyl acetate gave pure product (0.8 g, 26.5% yield); m.p. 161°–164° C.

Analysis calculated for $C_7H_8N_2O_2S_2$: N, 12.96; C, 38.87; H, 3.73. Found: N, 12.77; C, 38.87; H, 3.80.

EXAMPLE 7

2-Sulfamoyl-6-carbamoyl-4,5,6,7-tetrahydrothieno[2,3-c]pyridine

To a warm (40° C.) solution of 2-sulfamoyl-4,5,6,7-tetrahydrothieno[2,3-c]pyridine (1.42 g, 6.5 mmol) in acetonitrile (80 ml), under a nitrogen atmosphere, was added trimethylsilyl isocyanate (1.0 ml, 7.4 mmol). This solution was stirred for 19 hours and then methanol (2 ml) was added. After 2 hours the precipitated pure product was collected by filtration (1.62 g, 95% yield); m.p. 205°–208° C.

Analysis calculated for $C_8H_{11}N_3O_3S_2$: N, 16.08; C, 36.77; H, 4.24. N, 16.20; C, 36.77; H, 4.38.

EXAMPLE 8

2-Sulfamoyl-6-(2-hydroxyethyl)-4,5,6,7-tetrahydrothieno[2,3-c]pyridine

Into a solution of 2-sulfamoyl-4,5,6,7-tetrahydrothieno[2,3-c]pyridine (1.74 g, 8.0 mmol) in methanol (25 ml) and acetonitrile (50 ml) was bubbled ethylene oxide gas for 10 minutes. The reaction vessel was stoppered and the mixture was stirred for 18 hours. The precipitated product was collected by filtration. The filtrates were concentrated to provide additional product (total weight, 2.02 g). This material was crystallized from acetonitrile to give 1.67 g (80% yield) of pure product; m.p. 184°–186° C.

Analysis calculated for $C_8H_{11}N_3O_3S_2$: N, 10.68; C, 41.20; H, 5.38. Found: N, 10.93; C, 41.24; H, 5.44.

EXAMPLE 9

2-Sulfamoylthieno[2,3-c]pyridin-7(6H)-one

Step A: preparation of N,N-Dimethyl-N'-(thieno[2,3-c]pyridine-2-sulfonyl)-formamidine To a partial suspension of 2-sulfamoylthieno[2,3-c]pyridine (1.81 g, 8.5 mmol) in acetonitrile (20 ml), under a nitrogen atmosphere, was added dropwise dimethylformamide dimethyl acetal (1.3 ml, 9.7 mmol). After 2 hours, the mixture was diluted with chloroform, washed with water, dried over anhydrous sodium sulfate, filtered and evaporated to give 2.2 g of product. This material was recrystallized from ethyl acetate to give 2.05 g (90% yield); m.p. 169°–171° C. Analysis calculated for $C_{10}H_{11}N_3O_2S_2$: N, 15.60; C, 44.59; H, 4.12. Found: N, 15.79; C, 44.95; H, 4.08.

Step B: Preparation of N,N-Dimethyl-N'-(6-oxido-thieno-[2,3-c]pyridine-2-sulfonyl)formamidine To a solution of N,N-dimethyl-N'-(thieno[2,3-c]pyridine-2-sulfonyl)formamidine (2.05 g, 7.6 mmol) in chloroform (30 ml) was added dropwise a solution of m-chloroperbenzoic acid (1.82 g, 8.5 mmol) in ethyl acetate (17 ml). After stirring at room temperature for 18 hours, the precipitated product was collected on a filter. The filtrate was concentrated to obtain additional product. The combined material (2.08 g) was crystallized from chloroform to give 1.98 g (91% yield) of pure product; m.p. 237°–239° C.

Alternative Procedure

To a suspension of 2-sulfamoylthieno[2,3-c]pyridine-6-oxide (3.73 g, 16.2 mmol) in acetonitrile (50 ml) was added dropwise dimethylformamide dimethyl acetal (2.5 ml, 19 mmol). After stirring at room temperature for 18 hours, the precipitated product was collected on a filter. The filtrate was evaporated to obtain additional product. The combined material (4.36 g) was recrystallized from chloroform to give 3.64 g (79% yield) of pure product; m.p. 237°–239° C.

Analysis calculated for $C_{10}H_{11}N_3O_3S_2$: N, 14.73; C, 42.09; H, 3.89. Found: N, 14.81; C, 42.34; H, 3.86.

Step C: Preparation of N,N-Dimethyl-N'-(7-acetoxythieno[2,3-c]pyridine-2-sulfonyl)formamidine A mixture of N,N-dimethyl-N'-(6-oxido-thieno[2,3-c]pyridine-2-sulfonyl)formamidine (3.5 g, 12.3 mmol) in acetic anhydride (20 ml), under a nitrogen atmosphere, was heated at 120° C. for 3 hours. The dark solution was poured into ice/water and stirred for ½ hour. The product was extracted into methylene chloride, washed with sodium carbonate solution, dried over anhydrous sodium sulfate and evaporated to give 4.77 g of crude product. This residue was triturated with methylene chloride/diethyl ether to give 2.0 g (50% yield) of pure product. Recrystallization from ethyl acetate gave product with a broad melting point of 184°–191° C.

Analysis calculated for $C_{12}H_{13}N_3O_4S_2$: N, 12.84; C, 44.02; H, 4.00. Found: N, 12.63; C, 44.28; H, 4.22.

Step D: Preparation of 2-Sulfamoylthieno[2,3-c]pyridin-7(6H)-one

An initial suspension of N,N-dimethyl-N'-(7-acetoxythieno[2,3-c]pyridine-2-sulfonyl)formamidine (2.0 g, 6.1 mmol) in 10 N sodium hydroxide (4 ml) diluted with water (15 ml) was warmed at 60° C. for 1 hour. This clear solution was cooled and acidified with concentrated hydrochloric acid to give a precipitate of product. This precipitate (1.2 g) was collected by filtration and dried in a vacuum oven. Recrystallization by dissolution in a minimum amount of hot dimethyl sulfoxide, followed by dilution with ethanol gave 0.76 g (54% yield) of pure product; m.p. 295°–297° C.

Analysis calculated for $C_7H_6N_2O_3S_2$: N, 12.17; C, 36.51; H, 2.63. Found: N, 12.00; C, 36.49; H, 2.57.

EXAMPLE 10

2-Sulfamoylthieno[3,2-c]pyridine

The title compound was prepared according to the procedure described for 2-sulfamoylthieno[2,3-c]pyridine (Example 1) except thieno[3,2-c]pyridine was substituted for thieno[2,3-c]pyridine. This title compound was obtained in 41% yield; m.p. 193°–194° C., after crystallization from ethyl acetate.

Analysis calculated for $C_7H_6N_2O_2S_2$ : N, 13.08; C, 39.24; H, 2.82. Found: N, 13.10; C, 39.31; H, 2.86.

EXAMPLE 11

2-Sulfamoylthieno[3,2-c]pyridine-5-oxide

The title compound was prepared according to the procedure described for 2-sulfamoylthieno[2,3-c]pyridine-6-oxide (Example 3) except 2-sulfamoylthieno[3,2-c]pyridine was substituted for 2-sulfamoylthieno[2,3-c]pyridine. The title compound was obtained in 69% yield; m.p. 252°–254° C., after recrystallization from dimethyl sulfoxide/ethanol.

Analysis calculated for $C_7H_6N_2O_3S_2$: N, 12.17; C, 36.50; H, 2.64. Found: N, 11.99; C, 36.58; H, 2.73.

EXAMPLE 12

2-Sulfamoylthieno[3,2-c]pyridin-4(5H)-one

To a suspension of thieno[3,2-c]pyridin-4(5H)-one (1.51 g, 10 mmol) in distilled tetrahydrofuran (20 ml), cooled to −70° C. and under a nitrogen atmosphere, was added dropwise 0.7 M lithium diisopropylamide in THF (36 ml, 25 mmol). After one hour, sulfur dioxide gas was bubbled over the surface of this suspension and the reaction was allowed to gradually warm to room temperature. The mixture was diluted with diethyl ether and the precipitated lithium sulfinate intermediate was collected (3.6 g). This salt was dissolved in water (25 ml) and sodium acetate trihydrate (5.4 g, 66 mmol) and hydroxylamine-O-sulfonic acid (2.5 g, 22 mmol) were added. After stirring for 16 hours, the precipitated product was collected by filtration. The product was purified by recrystallization from hot dimethyl sulfoxide by dilution with ethanol to give 1.35 g (59% yield); m.p. 300°–301° C.

Analysis calculated for $C_7H_6N_2O_3S_2$: N, 12.17; C, 36.51; H, 2.63. Found: N, 12.08; C, 36.68; H, 2.62.

Alternate Procedure

Step A: Preparation of 2-Sulfamoyl-4-chlorothieno[3.2-c]pyridine

To a solution of 4-chlorothieno[3,2-c]pyridine (1.7 g, 10 mmol) in distilled tetrahydrofuran (25 ml), cooled to −70° C. and under a nitrogen atmosphere, was added dropwise 0.7 M lithium diisopropylamide in THF (16 ml, 11 mmol) to give a clear solution. After 178 hour, sulfur dioxide gas was bubbled over the reaction surface and it was gradually let warm to room temperature. The mixture was diluted with diethyl ether and the precipitated lithium sulfinate salt was collected by filtration. This salt (3.1 g) was dissolved in water (25 ml) and sodium acetate trihydrate (5.4 g, 66 mmol) and hydroxylamine-O-sulfonic acid (2.5 g, 22 mmol) were added. After stirring for 18 hours, the precipitated product was collected by filtration, dissolved in ethyl acetate, dried over anhydrous sodium sulfate, filtered through a pad of charcoal and the solvent was evaporated. The residue was recrystallized from ethyl acetate to give 1.23 g (49% yield) purified product.

Step B: Preparation of 2-Sulfamoylthieno[3,2-c]pyridin-4(5H)-one

A solution of 2-sulfamoyl-4-chlorothieno[3,2-c]pyridine (0.87 g, 3.5 mmol) in 10 N sodium hydroxide (1.8 ml) diluted with water (7 ml) was heated at 100° C. for 5-10 hours. After cooling the reaction and acidification with concentrated hydrochloric acid, the precipitated product was collected by filtration. Recrystallization from hot dimethyl sulfoxide by dilution with ethanol gives 0.53 g (66% yield) of product; m.p. 299°-301° C.

EXAMPLE 13

Thieno[2,3-b]pyridine-2-sulfonamide

A solution of thieno[2,3-b]pyridine (3.80 g, 0.028 mol) in THF (30 ml) was cooled to −70° C. under nitrogen. A solution of n-butyl lithium in hexane (1.6 M, 19.4 ml, 0.031 mol) was added dropwise while maintaining the internal temperature below −60° C. After a further 0.5 hour at this temperature, anhydrous $SO_2$ (g) was introduced over the surface of the reaction mixture for a period of one hour. The mixture was stirred for an additional hour, warmed to 20° C. and diluted with ether. The tan solid was collected and dried in vacuo at 25° C. to remove excess $SO_2$. This solid was suspended in methylene chloride and cooled to 0° C. N-Chlorosuccinimide (4.00 g, 0.030 mol) was added portionwise, maintaining the temperature below 10° C. The mixture was stirred one hour at 0° C. and one hour at 25° C. The solid was collected, washed with methylene chloride and the filtrate and washings were evaporated to give 6.5 g of the sulfonyl chloride. This material was dissolved in THF (25 ml) and added to a solution of concentrated aqueous ammonium hydroxide (15 ml) in acetone (65 ml) at 0°-10° C. After 0.25 hour, the solvent was evaporated and the residue was treated with water. After drying there was obtained 4.84 g (80% yield) of product; m.p. 223°-225° C. Recrystallization from isopropanol gave material with m.p. 224°-226° C.

Analysis calculated for $C_7H_6N_2O_2S_2$: N, 13.08; C, 39.24; H, 2.82. Found: N, 13.08; C, 39.73; H, 2.76.

EXAMPLE 14

2-Sulfamoylthieno[2.3-b]pyridine-7-oxide

A mixture of thieno[2,3-b]pyridine-2 Sulfonamide (0.43 g, 2 mmol) and 30% hydrogen peroxide (1.0 ml) in acetic acid (5.0 ml) was stirred at 55° C. for 24 hours. The reaction mixture was diluted with water, chilled and the resulting solid was collected and dried; 0.35 g (76% yield); m.p. 278°-279° C.

Analysis calculated for $C_7H_6N_2O_3S_2$: N, 12.17; C, 36.51; H, 2.63. Found: N, 12.44; C, 36.93; H, 2.51.

EXAMPLE 15

2-Sulfamoylthieno[2,3-b]pyridin-6-(7H)-one

Step A: N,N-Dimethyl-N′-(7-oxidothieno[2 3-b]pyridine-2-sulfonyl)formamidine A mixture of 2-sulfamoylthieno[2,3-b]pyridine-7-oxide (0.50 g, 2.2 mmol) and dimethylformamide dimethyl acetal (0.3 g, 2.2 mmol) in acetonitrile (3 ml) was stirred for 24 hours at 25° C. The solvent was evaporated and the residue was treated with water. After filtration and drying, there was obtained 0.57 g, (91%) m.p. 232°-234° C.

Analysis calculated for $C_{10}H_{11}N_3O_3S_2$: N, 14.73; C, 42.09; H, 3.89. Found: N, 14.83; C, 42.16; H, 3.97.

Step B: Preparation of 2-Sulfamoylthieno[2,3-b]pyridin-6(7H)-one

A mixture of the product from Step A (10.75 g, 0.038 mol) and 50 ml of acetic anhydride was heated at reflux for 16 hours. After removal of the acetic anhydride in vacuo, the residue was heated in 6 N hydrochloric acid (50 ml) for 3 hours. The cooled reaction mixture was diluted with water (400 ml), chilled and the resulting solid was filtered, washed with water and dried, 5.25 g (60% yield). Recrystallization from water gave 2-sulfamoylthieno[2,3-b]pyridin-6(7H)-one; m.p. 306°-308° C.

Analysis calculated for $C_7H_6N_2O_3S_2$: N, 12.17; C, 36.51; H, 2.63. Found: N, 12.16; C, 36.86; H, 2.68.

EXAMPLE 16

2-Sulfamoyl-6-[2-(dimethylamino)ethyl]thieno[2,3-c]pyridin-7(6H)-one Hydrochloride

Step A: Preparation of 6-[2-(Dimethylamino)ethyl]thieno[2,3-c]pyridin-7(6H)-one To a solution of thieno[2,3-c]pyridin-7(6H)one (2.92 g, 19.3 mmol) in dry dimethylformamide (20 ml) under a nitrogen atmosphere was added 2-(dimethylamino)ethyl chloride hydrochloride (3.15 g, 21.8 mmol). This mixture was warmed to 80° C. and sodium hydride in mineral oil (60%, 2.6 g, 65 mmol) was added carefully and rapidly. After 1.5 hours additional 2-(dimethylamino)ethyl chloride hydrochloride (1.45 g, 10 mmol) was added. After two hours the reaction mixture was cooled and diluted with water. The crude product was extracted into chloroform and then into dilute hydrochloric acid. The acidic solution was made basic with sodium hydroxide and the product extracted into diethyl ether. This was dried over anhydrous sodium sulfate, filtered and evaporated to give an oily product (3.8 g, 89% yield) which contained less than 10% of the by-product resulting from O-alkylation.

This material was further purified by formation of the hydrochloride salt upon treatment with ethanolic HCl.

Recrystallization from hot ethanol gave pure salt, m.p. 212°–214° C.

Analysis calculated for $C_{11}H_{14}N_2OS \cdot HCl$: N, 10.83; C, 51.05; H, 5.84. Found: N, 10.93; C, 51.02; H, 5.92.

Step B: Preparation of 2-Sulfamoyl-6-[2-(dimethylamino)ethyl]thieno[2,3-c]pyridin-7(6H)-one Hydrochloride To a solution of diisopropylamine (1.9 ml, 13.5 mmol) in distilled tetrahydrofuran (20 ml), under a nitrogen atmosphere, and cooled to −10° C., was added dropwise a solution of 1.55 M butyl lithium in hexane (8.8 ml, 13.5 mmol). After stirring for 20 minutes, a solution of 6-[(2-dimethylamino)ethyl]thieno[2,3-c]pyridin-7(6H)-one (2.65 g, 11.9 mmol) in tetrahydrofuran (20 ml) was added dropwise. After 1.5 hours, a gummy salt precipitated. Sulfur dioxide gas was bubbled over the surface of the reaction mixture to give a brown solid. Upon gradual warming to room temperature, the mixture was diluted with hexane and the precipitate was collected by filtration. This crude lithium sulfinate salt (5.8 g) was dissolved in water (35 ml) and sodium acetate trihydrate (11.2 g, 82 mmol) and hydroxylamine-O-sulfonic acid (3.06 g, 27 mmol) were added. After stirring for 15–20 hours the solution was made basic with saturated sodium carbonate. A little ethyl acetate was added to this gummy mixture and after stirring for 1–2 hours the precipitated product was isolated by filtration. This product (1.43 g, 40% yield) was partially suspended in methanol and excess ethanolic HCl was added. From the resultant solution, the product crystallized (1.51 g). Recrystallization from a large volume of hot methanol gave pure product (1.22 g), m.p. 262°–264° C.

Analysis calculated for $C_{11}H_{15}N_3O_3S_2 \cdot HCl$: N, 12.44; C, 39.10; H, 4.77. Found: N, 12.59; C, 39.26; H, 4.83.

EXAMPLE 17

2-Sulfamoyl-6-[3-(dimethylamino)propyl]thieno[2,3-c]pyridin-7(6H)-one Hydrochloride

Step A:

Preparation of 6-[3-(Dimethylamino)propyl]thieno[2,3-c]pyridin-7(6H)-one

To a solution of thieno[2,3-c]pyridin-7(6H)-one (1.82g, 12 mmol) in dry dimethylformamide (18 ml), under a nitrogen atmosphere, was added 3-(dimethylamino)propyl chloride hydrochloride (2.25 g, 14.4 mmol). Sodium hydride in mineral oil (60%, 1.35 g, 33 mmol) was carefully added to this solution and the mixture was warmed at 80° C. for 3 hours. The cooled reaction mixture was diluted with ice-water and the crude product was extracted into methylene chloride. This organic layer was extracted with dilute hydrochloric acid and the acid layer was made basic with sodium hydroxide solution. After extraction of the product into methylene chloride, this solution was dried over anhydrous sodium sulfate, filtered and evaporated to give an oily product (2.7 g, 95% yield) which contained less than 12% of the by-product resulting from O-alkylation. Some of this material was further purified by formation of the hydrochloride salt upon treatment with ethanolic HCl. Recrystallization from hot ethanol gave pure salt, m.p. 185°–190° C.

Analysis calculated for $C_{12}H_{16}N_2OS \cdot HCl$: N, 10.27; C, 52.83; H, 6.28. Found: N, 10.45; C, 52.61; H, 6.10.

Step B: Preparation of 2-Sulfamoyl-6-[3-(dimethylamino)propyl]thieno[2,3-c]pyridin-7(6H)-one Hydrochloride To a solution of diisopropylamine (1.4 ml, 10 mmol) in distilled tetrahydrofuran (15 ml), under a nitrogen atmosphere, and cooled below −25° C., was added dropwise a solution of 1.55 M n-butyl lithium in hexane (6.5 ml, 10 mmol). After 15 minutes, a solution of 6-[3-(dimethylamino)propyl]thieno[2,3-c]pyridin-7(6H)-one (2.05 g, 8.5 mmol) in tetrahydrofuran (15 ml) was added dropwise. After one-half hour sulfur dioxide gas was bubbled over the surface of the reaction and a light brown precipitate formed. Upon gradual warming, the mixture was diluted with hexane and the precipitate was collected by filtration. This crude lithium sulfinate salt (4.4 g) was dissolved in water (30 ml) and sodium acetate trihydrate (8.2 g, 60 mmol) and hydroxylamine-O-sulfonic acid (2.4 g, 21 mmol) were added. After stirring at room temperature for 20 hours the solution was made basic with saturated sodium carbonate. This solution was exhaustively extracted with ethyl acetate/methanol, dried over anhydrous sodium sulfate, filtered and the solvents evaporated to give a residue which upon trituration with diethyl ether/ethanol gave solid product (1.92 g, 72% yield). This product was dissolved in hot methanol and excess ethanolic HCl was added. Upon concentration of this solution the product salt crystallized (1.65 g). Recrystallization from hot methanol gave pure product (1.33 g), m.p. 151.5°–153.5° C.

Analysis calculated for $C_{12}H_{17}N_3O_3S_2 \cdot HCl$: N, 11.94; C, 40.96; H, 5.16. Found: N, 12.01; C, 41.21; H, 5.50.

EXAMPLE 18

2-Sulfamoyl-6-(3-cyanobenzyl)-4,5,6,7-tetrahydrothieno[2,3-c]pyridine

To a partial suspension of 2-sulfamoyl-4,5,6,7-tetrahydrothieno[2,3-c]pyridine (2.20 g, 10.1 mmol) in acetonitrile (50 ml) containing 3-cyanobenzylbromide (2.36 g, 12 mmol) was added triethylamine (1.70 ml, 12.2 mmol). After stirring at room temperature for three hours, the clear solution was diluted with water and the product was extracted into ethyl acetate/methanol, dried over anhydrous sodium sulfate, filtered and evaporated to give a residue which was triturated with methylene chloride/diethyl ether to give purified product (3.2 g, 96% yield). Recrystallization from hot ethanol gave product (2.4 g), m.p. 137°–139° C.

Analysis calculated for $C_{15}H_{15}N_3O_2S_2$: N, 12.60; C, 54.03; H, 4.53. Found: N, 12.65; C, 54.32; H, 4.50.

EXAMPLE 19

2-Sulfamoyl-5-hydroxythieno[2,3-b]pyridine

To a solution of 5-hydroxythieno[2,3-b]pyridine (1.56 g, 10.3 mmol) in dry tetrahydrofuran (50 ml), under a nitrogen atmosphere and cooled to −10° C., was added dropwise 1.55M butyl lithium in hexane (15 ml, 23 mmol). After stirring for one hour, sulfur dioxide gas was bubbled over the reaction surface to give a white precipitate. Upon gradual warming to room temperature, the suspension was diluted with hexane and the precipitate collected by filtration. This crude lithium sulfinate salt (3.95 g) was dissolved in water (45 ml) and sodium acetate trihydrate (10.1 g, 74 mmol) and hydroxylamine-O-sulfonic acid (2.73 g, 24 mmol) were added. After stirring for 20 hours, the precipitated product was collected by filtration (1.29 g, 54% yield).

Recrystallization from hot ethyl acetate/methanol gave pure product (0.99 g), m.p. 271°–273° C.

Analysis calculated for $C_7H_6N_2O_3S_2$: N, 12.17; C, 36.51; H, 2.63. Found: N, 12.44; C, 36.82; H, 2.83.

Alternate procedure: The acidic filtrate from Example 15, Step B was neutralized with sodium hydroxide solution and saturated sodium carbonate solution to pH 7, followed by extraction with ethyl acetate (3×300 ml). The combined extracts were washed with water, saturated sodium chloride solution and dried ($Na_2SO_4$). The dried filtrate was evaporated to give 2.75 g (31% yield) of pale orange solid. Recrystallization from water followed by recrystallization from isopropanol gave 5-hydroxy-thieno[2,3-b]pyridine-2-sulfonamide; m.p. 270°–271°.

EXAMPLE 20

2-Sulfamoylthieno[3,2-b]pyridine

To a solution of thieno[3,2-b]pyridine (3.7 g, 27.4 mmol) in dry tetrahydrofuran (30 ml), under a nitrogen atmosphere, cooled to −30° C. was added 1.55 M n-butyl lithium in hexane (18.4 ml, 28.5 mmol). After stirring for one hour sulfur dioxide gas was bubbled over the surface of the reaction mixture to give a rust colored precipitate. The mixture was allowed to warm to room temperature, was diluted with hexane and the tan precipitate was collected by filtration. This lithium sulfinate salt (6.0 g) was dissolved in water (40 ml) and sodium acetate trihydrate (12.2 g, 90 mmol) and hydroxylamine-O-sulfonic acid (3.45 g, 30.5 mmol) were added. After stirring for 16 hours, precipitated product was collected by filtration, redissolved in ethyl acetate/methanol, dried over anhydrous sodium sulfate, filtered through a pad of charcoal and the solvent was evaporated to give product (4.08 g, 70% yield). It was recrystallized from hot ethyl acetate/methanol to give a pure product (2.45 g), m.p. 209°–211° C.

Analysis calculated for $C_7H_6N_2O_2S_2$: N, 13.08; C, 39.24; H, 2.82. Found: N, 13.28; C, 39.12; H, 2.81.

EXAMPLE 21

2-Sulfamoylthieno[3,2-]pyridine-4-oxide

To a suspension of 2-sulfamoylthieno[3,2-b]pyridine (2.95 g, 13.7 mmol) in glacial acetic acid (25 ml) warmed at 55° C. was added 30% hydrogen peroxide (2 ml, 17.7 mmol). This mixture was warmed for three hours and then allowed to stir at room temperature for 20 hours. The reaction mixture was diluted with water and the precipitate collected by filtration to give pure product (2.42 g, 77% yield), m.p 272.5°–273.5° C.

Analysis calculated for $C_7H_6N_2O_3S_2$: N, 12.17; C, 36.51; H, 2.63. Found: N, 12.37; C, 36.76; H, 2.98.

EXAMPLE 22

2-Sulfamoylthieno[3,2-b]pyridin-5(4H)-one

Step A: Preparation of N,N-Dimethyl-N'-(4-oxido-thieno-[3,2-b]pyridine-2-sulfonyl)formamidine To a partial suspension of 2-sulfamoylthieno[3,2-b]pyridine-4-oxide (1.64 g, 7.1 mmol) in acetonitrile (45 ml), under a nitrogen atmosphere at room temperature was added dimethylformamide dimethyl acetal (1.5 ml, 11 mmol). The product began to precipitate after initial complete solution. After stirring for 18 hours, the reaction mixture was diluted with chloroform to dissolve the product. The solution was washed with water, dried over anhydrous sodium sulfate, filtered through charcoal and evaporated to give nearly pure product (1.9 g, 94% yield). Recrystallization from hot chloroform gave pure product (1.6 g), m.p. 224°–225.5° C.

Analysis calculated for $C_{10}H_{11}N_3O_3S_2$: N, 14.73; C, 42.09; H, 3.89. Found: N, 14.94; C, 42.00; H, 4.00.

Step B: Preparation of 2-Sulfamoylthieno[3,2-b]pyridin-5(4H)-one

A suspension of N,N-dimethyl-N'-(4-oxido-thieno[3,2-b]pyridine-2-sulfonyl)formamidine (6.23 g, 22.6 mmol) in acetic anhydride (70 ml), under a nitrogen atmosphere, was heated at 140° C. for 20–22 hours to give a dark solution. The excess acetic anhydride was removed on a rotary evaporator and 6 N HCl (90 ml) was added to the residue and it was warmed at 80° C. for four hours. This reaction mixture was cooled and ice water was added as product began to precipitate. Upon standing several crops were collected by filtration. The combined crude product (2.2 g) was dissolved in a large volume of boiling water, filtered and allowed to cool. Pure product was obtained (1.72 g, 33% yield). This material was recrystallized by dissolution in a minimum volume of hot dimethylsulfoxide. This solution was treated with charcoal, filtered, and diluted with ethanol as product crystallized (1.3 g), m.p. >300° C.

Analysis calculated for $C_7H_6N_2O_3S_2$: N, 12.17; C, 36.51; H, 2.63. Found: N, 11.86; C, 36.81; H, 2.89.

EXAMPLE 23

2-Sulfamoyl-6-methoxythieno[3.2-b]pyridine

Step A: Preparation of 6-Acetylthieno[3,2-b]pyridine oxime

To a solution of 6-acetylthieno[3,2-b]pyridine (3.78 g, 21.3 mmol) in pyridine (40 ml) and ethanol (40 ml), under a nitrogen atmosphere, was added hydroxyl amine hydrochloride (5.0 g, 72 mmol). After the reaction mixture was heated at 80° C. for three hours, the solvents were removed under reduced pressure on a rotary evaporator and the residue was diluted with ice water to give crystalline product. This solid was collected by filtration and dissolved in ethyl acetate/methanol, dried over anhydrous sodium sulfate and filtered through charcoal. The solvents were evaporated to give pure product (3.15 g, 77% yield) which was used as is. A small portion was recrystallized from methanol for microanalysis, m.p 210°–213° C.

Analysis calculated for $C_9H_8N_2OS$: N, 14.58; C, 56.23; H, 4.19. Found: N, 14.97; C, 56.52; H, 4.28.

Step B: Preparation of 6-Acetamidothieno[3,2-b]pyridine

To a suspension of 6-acetylthieno[3,2-b]pyridine oxime (3.3 g, 17.2 mmol) in dry benzene (50 ml), under a nitrogen atmosphere, there was added in one portion, with vigorous stirring, phosphorus pentachloride (4.3 g, 20.7 mmol). This mixture was gradually warmed to 80° C. over ½ hour and then cooled and poured into ice/water and made weakly basic with sodium hydroxide solution. The precipitated product was extracted into ethyl acetate/methanol, washed with water, dried over anhydrous sodium sulfate and the solution was filtered through a pad of charcoal and concentrated to dryness. The residue was triturated with diethyl ether and the product collected by filtration (2.92 g, 88% yield) and used as is. A small portion was recrystallized from ethyl acetate/methanol for microanalysis, m.p. 192°–194° C.

Analysis calculated for $C_9H_8N_2OS$: N, 14.58; C, 56.23; H, 4.19. Found: N, 14.70; C, 56.46; H, 4.17.

Step C: Preparation of 6-Aminothieno[3,2-b]pyridine

A suspension of 6-acetamidothieno[3,2-b]pyridine (2.29 g, 12 mmol) in ethanol (35 ml) and concentrated hydrochloric acid (15 ml) was warmed at 80° C. for two hours. This mixture was diluted with water and made basic by the addition of sodium hydroxide solution. The product was extracted into methylene chloride, dried over anhydrous sodium sulfate and then filtered through a pad of charcoal and the solvent was evaporated to give pure product (1.36 g, 76% yield), m.p. 121°–123° C.

Analysis calculated for $C_7H_6N_2S$: N, 18.65; C, 55.97; H, 4.03. Found: N, 18.33, C, 56.23; H, 4.09.

Step D: Preparation of 6-Hydroxythieno[3,2-b]pyridine

To a solution of 6-aminothieno[3,2-b]pyridine (2.5 g, 16.6 mmol) in water (22 ml) containing concentrated sulfuric acid (4.15 ml) and cooled at 0° C. was added dropwise with vigorous stirring a solution of sodium nitrite (1.26 g, 18.3 mmol) in water (7 ml) to give a copious yellow precipitate. This slurry was pipetted dropwise into 5% sulfuric acid (110 ml) maintained at 110° C. After an additional hour, the solution was cooled to room temperature and washed with methylene chloride. This aqueous solution was made basic with sodium hydroxide and washed again with methylene chloride to remove any unreacted starting material. The aqueous solution was then made neutral with hydrochloric acid and the precipitated product was extracted into chloroform/methanol, dried over anhydrous sodium sulfate and filtered through a pad of charcoal and the solvents were evaporated to give product (2.2 g) which was purified by crystallization from hot ethyl acetate/methanol to give pure product (1.81 g, 72% yield), m.p. 228°–230° C.

Analysis calculated for $C_7H_5NOS$: N, 9.27; C, 55.61; H, 3.33. Found: N, 9.44; C, 55.54; H, 3.31.

Step E: Preparation of 6-Methoxythieno[3,2-b]pyridine

To a solution of 6-hydroxythieno[3,2-b]pyridine (2.45 g, 16.2 mmol) in dry dimethylsulfoxide (15 ml), under a nitrogen atmosphere, was added 60% sodium hydride in mineral oil (0.75 g, 19 mmol) and let stir at room temperature for 1 hour. Methyl iodide (1.25 ml, 21 mmol) was added to this solution and it was stirred for an additional two hours. The solution was poured into ice/water and extracted with diethyl ether, washed with water, dried over anhydrous sodium sulfate, filtered and carefully evaporated to give an oily product (2.1 g, 78% yield) which was used as is.

Step F: Preparation of 2-Sulfamoyl-6-methoxythieno[3,2-b]pyridine

To a solution of crude 6-methoxythieno[3,2-b]pyridine (1.8 g, 11 mmol) in distilled tetrahydrofuran (15 ml), under a nitrogen atmosphere and cooled below −30° C., was added dropwise 1.6 M butyl lithium in hexanes (7.0 ml, 11.2 mmol) to give a dark gummy precipitate. After 178 hour, sulfur dioxide gas was bubbled over the reaction surface to give a brownish powdery precipitate. After the mixture warmed to room temperature, the mixture was diluted with hexane. The crude precipitated lithium sulfinate salt was collected by filtration, washed with diethyl ether and air dried. This salt (2.45 g) was dissolved in water (23 ml) and sodium acetate trihydrate (5.9 g, 39 mmol) and hydroxylamine-O-sulfonic acid (1.47 g, 13 mmol) were added and the solution was stirred for 16 hours. The precipitated product was collected by filtration, dissolved in ethyl acetate/methanol, dried over anhydrous sodium sulfate and then filtered through a pad of charcoal. The residue after evaporation of the filtrate was triturated with diethyl ether and the product (1.33 g, 50% yield) was collected by filtration. Crystallization from ethyl acetate/methanol qave pure product (1.1 g), m.p. 210°–212° C.

Analysis calculated for $C_8H_8N_2O_3S_2$: N, 11.47; C, 39.33; H, 3.46. Found: N, 11.30; C, 39.52; H, 3.28.

EXAMPLE 24

2-Sulfamoyl-6-hydroxythieno[3,2-b]pyridine

A mixture of 2-sulfamoyl-6-methoxythieno[3,2-b]pyridine (512 mg, 2.1 mmol) and pyridine hydrochloride (1.62 g, 14 mmol), under a nitrogen atmosphere, was placed in an oil bath heated at 190° C. for ¾ hour. The cooled mixture was diluted with water as the product slowly crystallized out. The mixture was extracted into ethyl acetate/methanol, washed with water, dried over anhydrous sodium sulfate, filtered through a pad of charcoal and evaporated. The residue was triturated with diethyl ether and the product was collected by filtration (330 mg, 68% yield). Crystallization from hot ethyl acetate/methanol by boiling off the methanol gave pure product, m.p. 248°–250° C.

Analysis calculated for $C_7H_6N_2O_3S_2$; N, 12.17; C, 36.51; H, 2.63. Found: N, 11.99; C, 36.80; H, 2.60.

Alternate Procedure

To a suspension of 6-hydroxythieno[3,2-b]pyridine (1.82 g, 12 mmol) in distilled tetrahydrofuran (60 ml), under a nitrogen atmosphere and cooled to −10° C., was added dropwise 1.55 M butyl lithium in hexane (17 ml, 26.3 mmol). After 1–2 hours, sulfur dioxide gas was bubbled over the reaction surface giving a lighter yellow precipitate. After warming the mixture to room temperature, it was diluted with hexane, and the precipitate was collected by filtration. This crude lithium sulfinate salt (4.5 g) was dissolved in water (55 ml) and sodium acetate trihydrate (11.0 g, 81 mmol) and hydroxylamine-O-sulfonic acid (3.1 g, 27 mmol) were added. After stirring at room temperature for 16–20 hours, the precipitated product was collected by filtration, dissolved in ethyl acetate/methanol, dried over anhydrous sodium sulfate, filtered through a pad of charcoal and evaporated. This crude material (2.7 g) which consisted of two products by thin layer chromatography was chromatographed on silica gel (95 g) eluting with 2–12% methanol/chloroform. The faster moving and major product was isolated and crystallized from ethyl acetate and identified by proton coupling experiments to be 3-sulfamoyl-6-hydroxythieno[3,2-b]pyridine (835 mg, 30% yield), m.p. 245°–247° C. The minor, more polar, material was the desired product (290 mg, 10.5% yield).

Second Alternate Procedure

The acidic aqueous filtrate from the preparation of 2-sulfamoylthieno[3,2-b]pyridin-5(4H)-one (Step 2, Example 22) was made neutral with base and exhaustively extracted with ethyl acetate/methanol. The extracts were dried over anhydrous sodium sulfate, filtered through a pad of charcoal and the filtrate was evaporated. The residue was triturated with diethyl ether to give nearly pure product (0.50 g, 9.6% yield).

EXAMPLE 25

2-Sulfamoyl-5-methylthieno[3,2-b]pyridine

To a solution of a mixture of 5- and 7-methylthieno[3,2-b]pyridines (4:1 ratio, 9.1 g, 61 mmol) in dry tetrahydrofuran (60ml) under a nitrogen atmosphere and cooled below −30° C. was added 1.6 M butyl lithium (40 ml, 64 mmol). After stirring for 20 minutes, sulfur dioxide gas was bubbled over the reaction surface for one-half hour to give a brown solid. After warming to room temperature the reaction mixture was diluted with hexane. The precipitated crude lithium sulfinate salt was collected by filtration, washed with diethyl ether and air dried. This hydroscopic salt (24 g) was dissolved in water (60 ml) and sodium acetate trihydrate (26.6 g, 0.195 mol) and hydroxylamine-O-sulfonic acid (7.4 g, 65 mmol) were added. After stirring for 16 hours precipitated product was collected by filtration, redissolved in ethyl acetate/methanol, dried over anhydrous sodium sulfate, filtered through a pad of charcoal and evaporated to dryness to give only the 5-methyl isomer (4.5 g, 32% yield). Recrystallization twice from hot ethyl acetate/methanol gave pure product (2.5 g), m.p. 254°–255° C.

Analysis calculated for $C_8H_8N_2O_2S_2$: N, 12.27; C, 42.09; H, 3.53. Found: N, 12.24; C, 42.01; H, 3.43.

EXAMPLE 26

7-Methyl-2-sulfamoylthieno[3,2-b]pyridine

The aqueous filtrate from the reaction for the preparation of 2-sulfamoyl-5-methylthieno[3,2-b]pyridine (Example 25) was made neutral and extracted with ethyl acetate/methanol. This organic extract was dried over anhydrous sodium sulfate, filtered through a pad of charcoal and evaporated to give a residue which was triturated with diethyl ether to give a 3:2 mixture of 5- and 7-methyl-2-sulfamoylthieno[3,2-b]pyridine (0.63 g). The 7-methyl isomer was obtained pure by reverse phase high performance liquid chromatography. Recrystallization from hot ethyl acetate/methanol gave pure product (0.11 g), m.p. 230°–232° C.

Analysis calculated for $C_8H_8N_2O_2S_2$: N, 12.27; C, 42.09; H, 3.53. Found: N, 12.55; C, 42.25; H, 3.65.

EXAMPLE 27

| 2-Sulfamoylthieno[3,2-b]pyridine | 1 mg | 15 mg |
|---|---|---|
| Monobasic sodium phosphate 2H₂O | 9.38 mg | 6.10 mg |
| Dibasic sodium phosphate.12H₂O | 28.48 mg | 16.80 mg |
| Benzalkonium chloride | 0.10 mg | 0.10 mg |
| Water for injection q.s. ad. | 1.0 ml | 1.0 ml |

The novel compound, phosphate buffer salts, and benzalkonium chloride are added to and dissolved in water. The pH of the composition is adjusted to 6.8 and diluted to volume. The composition is rendered sterile by ionizing radiation.

EXAMPLE 28

| 2-Sulfamoylthieno[2,3-c]pyridine | 5 mg |
|---|---|
| petrolatum q.s. ad. | 1 gram |

The compound and the petrolatum are aseptically combined.

EXAMPLE 29

| 2-Sulfamoylthieno[2,3-c]pyridine | 1 mg |
|---|---|
| Hydroxypropylcellulose q.s. | 12 mg |

Ophthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrate insert are then autoclaved at 250° F. for ½ hour.

What is claimed is:

1. A compound of structural formula:

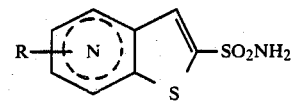

or N-oxide, or an ophthalmologically acceptable salt thereof wherein

is a pyrido, dihydropyrido or tetrahydropyrido group with the N at the 4-, 5-, 6- or 7-position; and R is (1) $C_{1-5}$ alkyl, either straight chain, branched chain or cyclic, (2) hydroxy-$C_{1-5}$ alkyl, (3) —$OR^1$, wherein $R^1$ is hydrogen, $C_{1-3}$ alkyl, cyclopropyl, amino-$C_{1-3}$ alkyl, $C_{1-3}$ alkylamino-$C_{1-3}$ alkyl, di($C_{1-3}$ alkyl)amino-$C_{1-3}$ alkyl, hydroxy-$C_{1-3}$ alkyl, or $C_{2-4}$ alkanoyl, (4)

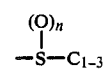

alkyl, wherein n is 0, 1 or 2, (5) —$N(R^1)_2$ wherein the $R^1$ groups can be the same or different, (6) halo selected from the group consisting of chloro, bromo or fluoro, (7) hydrogen, (8) —$NO_2$, or (9) oxo—; and if

is dihydro- or tetrahydropyrido, the N can be substituted with $R^1$ or $CONH_2$.

2. The compound of claim 1, wherein R is hydrogen, hydroxy, or di($C_{1-3}$ alkyl)amino-$C_{1-3}$ alkyl.

3. The compound of claim 2, which is:
2-Sulfamoylthieno[2,3-c]pyridine;
2-Sulfamoylthieno[3,2-c]pyridine;
2-Sulfamoylthieno[3,2-b]pyridine;
2-Sulfamoyl-5-hydroxythieno[2,3-b]pyridine;
2-Sulfamoyl-6-hydroxythieno[3,2-b]pyridine; or an ophthalmologically acceptable salt thereof.

4. A ophthalmological formulation for treating elevated intraocular pressure comprising an ophthalmologically acceptable carrier and an effective intraocular pressure lowering amount of the compound of claim 1 or an ophthalmologically acceptable salt thereof.

5. The formulation of claim 4, wherein R is hydrogen, hydroxy, or di($C_{1-3}$ alkyl)amino-$C_{1-3}$ alkyl.

6. The formulation of claim 5, wherein the compound is:
2-Sulfamoylthieno[2,3-c]pyridine;
2-Sulfamoylthieno[3,2-c]pyridine;
2-Sulfamoylthieno[3,2-b]pyridine;
2-Sulfamoyl-5-hydroxythieno[2,3-b]pyridine;
2-Sulfamoyl-6-hydroxythieno[3,2-b]pyridine; or an ophthalmoloqically acceptable salt thereof.

7. A method of treating elevated intraocular pressure which comprises the administration to a patient in need of such treatment of an effective intraocular pressure lowering amount of the compound of claim 1.

8. The method of claim 7, wherein R is hydrogen, hydroxy, or di($C_{1-3}$ alkyl)amino-$C_{1-3}$ alkyl.

9. The method of claim 8, wherein the compound is:
2-Sulfamoylthieno[2,3-c]pyridine;
2-Sulfamoylthieno[3,2-c]pyridine;
2-Sulfamoylthieno[3,2-b]pyridine;
2-Sulfamoyl-5-hydroxythieno[2,3-b]pyridine;
2-Sulfamoyl-6-hydroxythieno[3,2-b]pyridine; or an ophthalmologically acceptable salt thereof.

* * * * *